United States Patent [19]

Kienholz

[11] Patent Number: 5,415,282

[45] Date of Patent: May 16, 1995

[54] THERMAL STORAGE AND/OR SHIPPING CONTAINER WITH LEAK-RESISTANT BAG

[75] Inventor: Charles A. Kienholz, Erie, Pa.

[73] Assignee: Erie Steel Products Company, Erie, Pa.

[21] Appl. No.: 296,325

[22] Filed: Aug. 25, 1994

Related U.S. Application Data

[63] Continuation of Ser. No. 61,120, May 13, 1993, abandoned.

[51] Int. Cl.⁶ .............................................. F25D 3/00
[52] U.S. Cl. .................................. 206/216; 206/569; 206/524.4
[58] Field of Search ............... 206/216, 223, 569, 570, 206/585, 443, 524.3, 524.4; 62/457.2, 60, 271

[56] References Cited

U.S. PATENT DOCUMENTS

| | | |
|---|---|---|
| 662,541 | 11/1900 | Miskolczy . |
| 3,365,911 | 1/1968 | Stoner et al. . |
| 3,802,220 | 4/1974 | Pompo . |
| 4,281,520 | 8/1981 | Norwood . |
| 4,311,022 | 1/1982 | Hall . |
| 4,530,816 | 7/1985 | Douglas-Hamilto . |
| 4,580,412 | 4/1986 | Wells . |
| 4,596,250 | 6/1986 | Beisang et al. . |
| 4,619,678 | 10/1986 | Rubin ................................. 62/457.2 |
| 4,628,705 | 12/1986 | Nave . |
| 4,723,974 | 2/1988 | Ammerman . |
| 4,777,930 | 10/1988 | Hartz . |
| 4,932,533 | 6/1990 | Collier ................................. 206/569 |
| 4,985,232 | 1/1991 | Jacobssen ........................... 206/569 |
| 5,058,397 | 10/1991 | MacDonald ....................... 62/457.2 |
| 5,181,394 | 1/1993 | Schea et al. ........................ 206/570 |
| 5,236,088 | 8/1993 | Dhority et al. ................... 206/524.4 |

Primary Examiner—Jacob K. Ackun
Attorney, Agent, or Firm—Howson and Howson

[57] ABSTRACT

A combination thermal shipping and/or storage container and leak-resistant bag for potentially infectious biological specimens. Two molded plastic sections press together to form a closed compartment. A slow-warming or slow-cooling composition within each section surrounds the compartment to hold the specimens in the bag within a desired temperature range for a relatively long period. A portion of the bag extends from the closed container sections for exposing any labeling imprinted on the bag. A separate pouch in the bag, accessible from outside the container, is provided for holding any documentation which is to accompany the specimens.

28 Claims, 4 Drawing Sheets

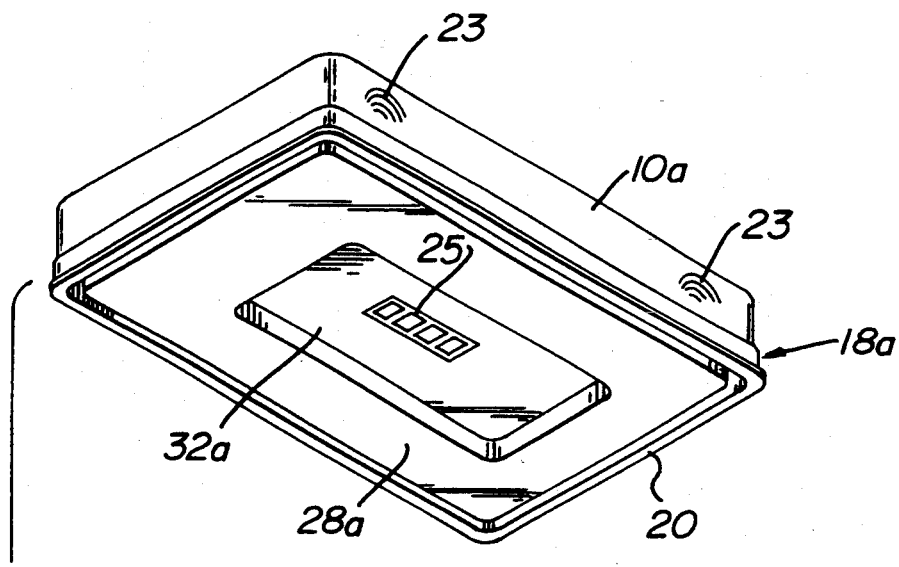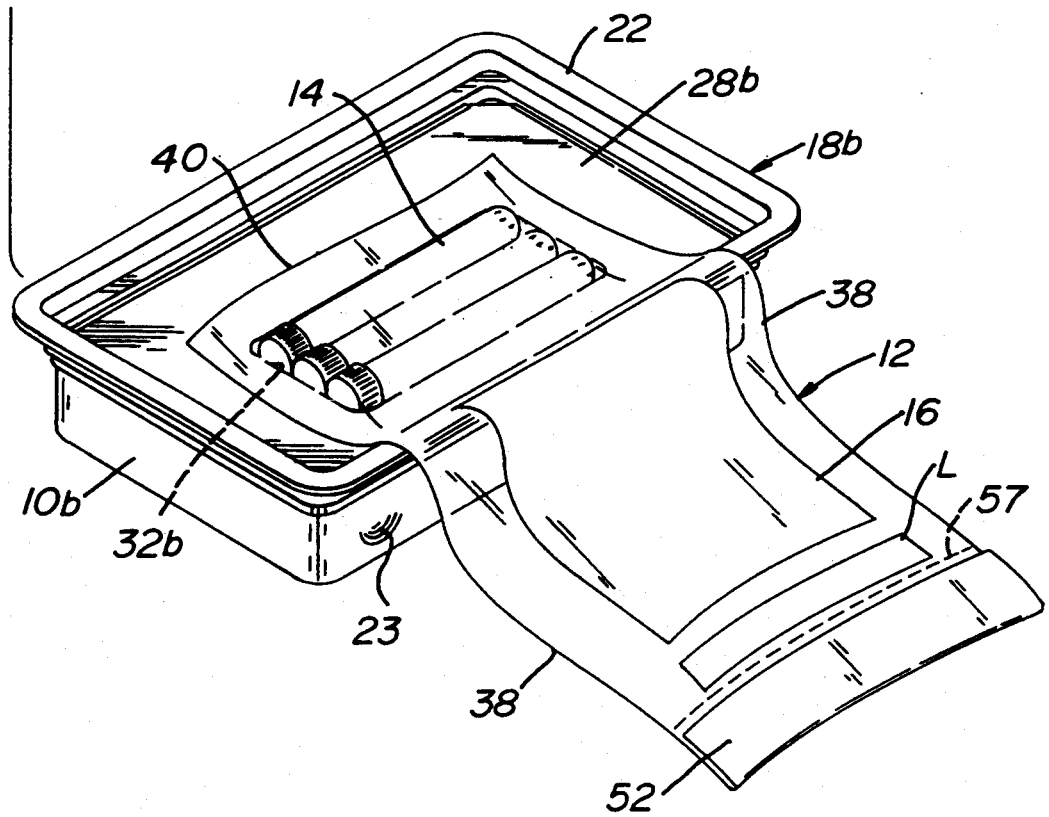
FIG.2

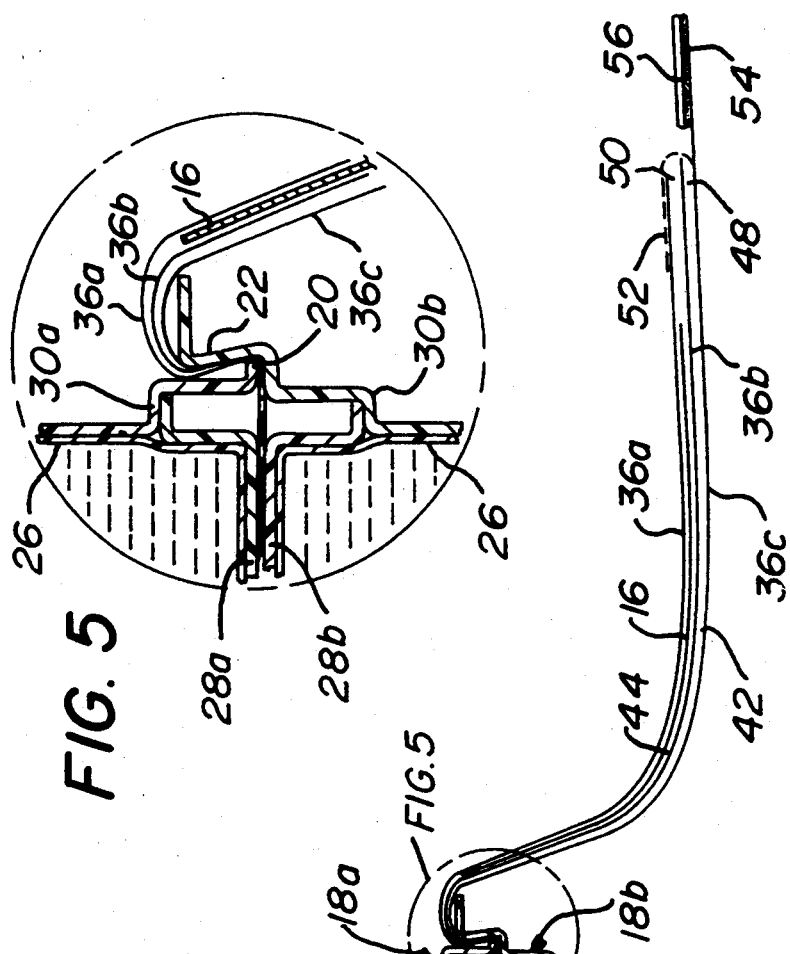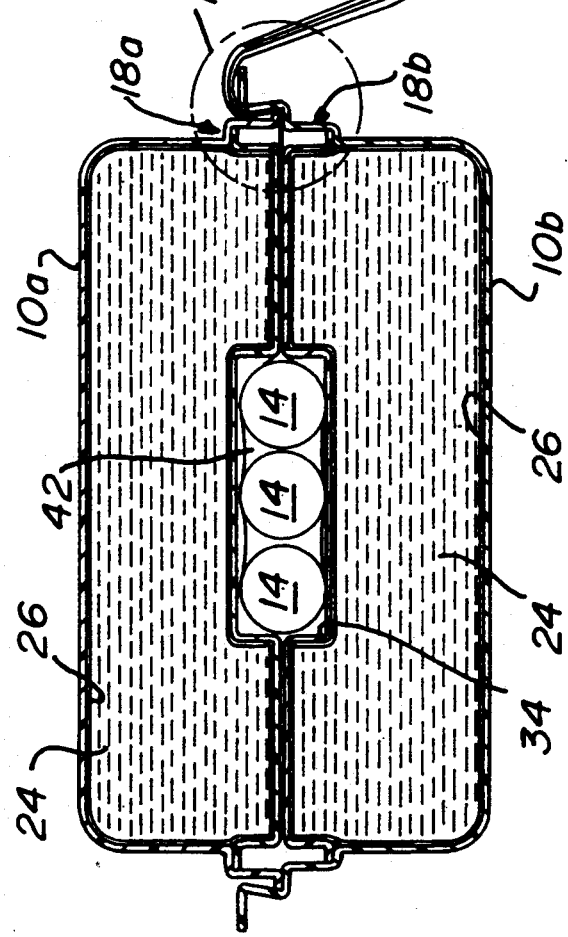

THERMAL STORAGE AND/OR SHIPPING CONTAINER WITH LEAK-RESISTANT BAG

This is a continuation of application Ser. No. 08/061,120 filed on May 13, 1993, and now abandoned.

BACKGROUND OF THE INVENTION

The present invention relates generally to thermal enclosures, and more particularly to a novel and improved combination thermal storage and/or shipping container and leak-resistant containment bag for maintaining blood specimens and other potentially infectious materials at a given temperature for extended periods.

The procedures for handling and storage of blood, urine and similar specimens collected in a doctor's office or clinic for transfer by a courier to a laboratory for testing vary widely depending on the nature of the specimen, temperature constraints, storage time before they are picked up by the courier, and the storage facilities at the doctor's office and provided by the courier service. For instance, containers of non-critical specimens, which can be stored at room temperature, may be placed directly in a lock box located inside or outside the doctor's office for pick-up. Blood specimens, on the other hand, are usually collected in vials by a technician and placed in a typical household freezer operating in the range of approximately −10° F. to 10° F. If courier pick-up is immediate or the same day before office closing, the frozen or partially frozen specimens are transferred directly to a freezer or dry ice container in the courier's van. However, if pick-up is after office hours, frozen specimens would be transferred to a specially designed insulated lock box located in an area outside the office accessible to the courier. If the lock box is at room or ambient temperature, there is the danger that the specimens will begin to thaw out before the courier arrives.

Extra precautions against leakage are required if the specimens are blood or other potentially infectious biological materials to which exposure can cause serious diseases in humans. If outside contamination of their primary container can occur, the Standards for Bloodborne Pathogens under the Occupational Safety and Health Act (OSHA) require (1) that the material be placed within a secondary container for protection against leakage during handling, processing, storage, transport or shipping, and (2) that the secondary container be properly labeled or color-coded to warn handlers of its contents. In addition, identification documents are usually enclosed with the materials in the secondary container along with instructions as to the tests to be performed.

Heretofore, prior art containers for storage and/or shipping biological specimens, which meet the OSHA standards for potentially infectious materials, have not been available. For instance, the container disclosed in U.S. Pat. No. 3,802,220 is not a leak-resistant container suitable for infectious materials.

SUMMARY OF THE INVENTION

Accordingly, it is an object of the present invention to provide a combination container and leak-resistant containment bag for temporary storage and/or transport of potentially infectious materials while maintaining the temperature of the materials within a selected range over a long period.

Still another object is to provide a thermal storage and shipping container designed to comply with present requirements of the Standards for Bloodborne Pathogens of the Occupational Health and Safety Act for potentially hazardous medical specimens, and to harmonize with present medical laboratory practices.

Another object is to provide a thermal storage and/or shipping container with a containment bag in which labels and accompanying documents pertaining to the contents of the container are prominently displayed and readily accessible without opening the container.

A still further object is to provide a thermal enclosure which is durable, reliable and inexpensive to manufacture.

These and other objects of the invention are accomplished by a combination container and leak-resistant containment bag for temporarily storing and shipping potentially infectious biological specimens or like materials. In one embodiment, the container is constructed of two complementary molded plastic hollow sections in which their outer edges snap together under positive pressure to form a box-like enclosure. A pouch of a slow-warming or slow-cooling composition is compressed contiguously within each section by a molded plastic wall. The facing sides of the walls are indented to form a central storage compartment of a size suitable for a snug fit of the materials in the containment bag. The bag may comprise two rectangular pouches for holding the materials, and identifying documents and any instructions pertaining thereto. The bag is of sufficient length for a portion, which includes the sealable openings, to extend from one side of the closed container and expose any labeling imprinted on the bag. In another embodiment the container has is a double wall bottom section with an open top, and a double wall cover section which press fits into the open top. The cavities formed between the walls are filled with a composition having a relatively high thermal inertia.

BRIEF DESCRIPTION OF THE DRAWINGS

For a more complete understanding and appreciation of the invention and many of its attendant advantages, reference will be made to the following detailed description taken in conjunction with the accompanying drawings, wherein:

FIG. 2 is a perspective view of the container of FIG. 1 shown opened with specimen tubes and a document in the containment bag;

FIG. 4 represents in transverse cross-section the container and bag of FIG. 1;

FIG. 5 is an enlargement of the encircled portion of the container and bag shown in FIG. 4.

DESCRIPTION OF THE PREFERRED EMBODIMENTS

Figure 1:
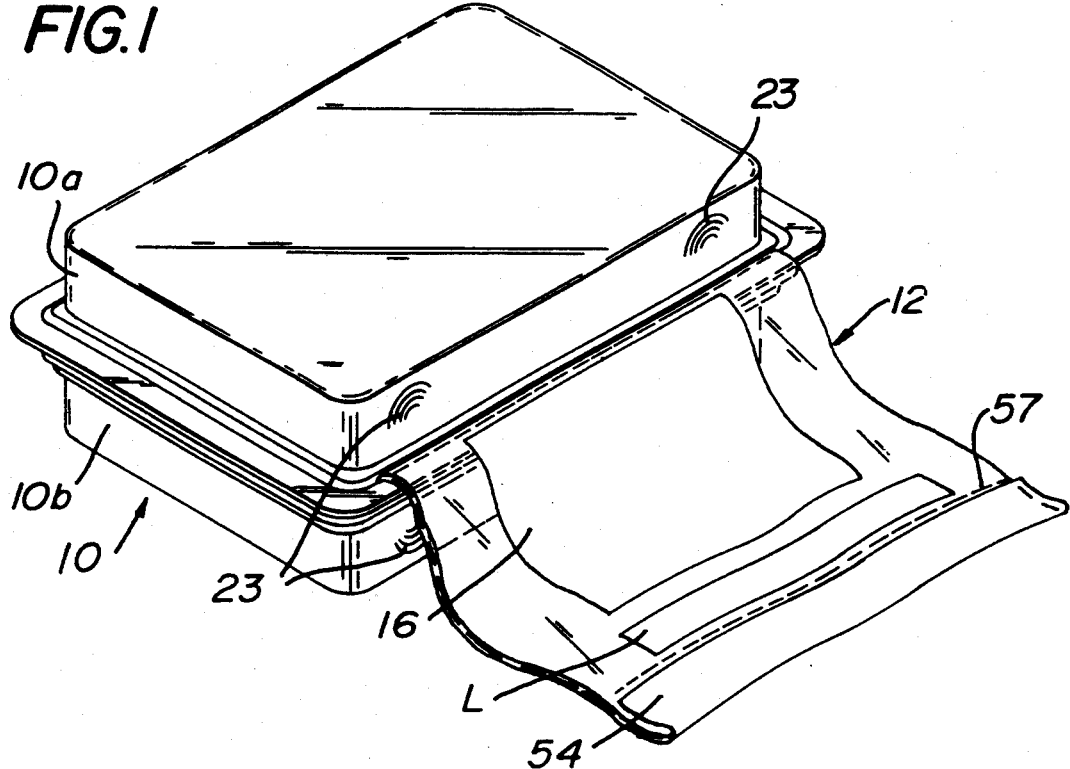
FIG. 1 is a perspective view of one embodiment of a combination thermal storage and/or shipping container and leak-resistant containment bag according to the invention with the container shown closed and a portion of the bag extending from one side.
Figure 3:
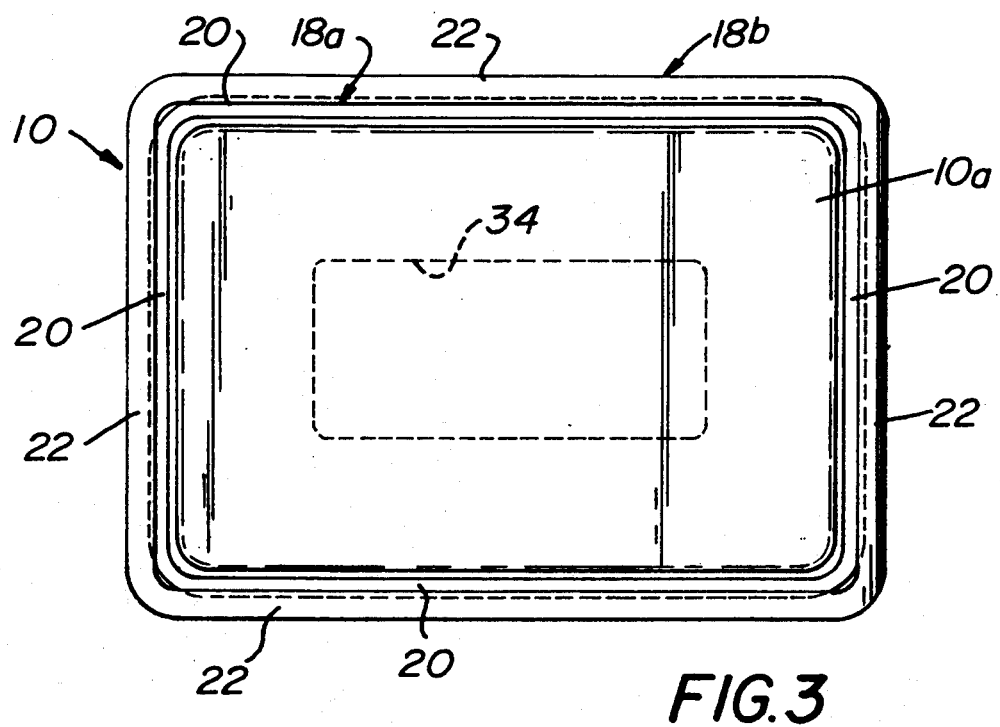
FIG. 3 is a plan view of the closed container of FIG. 1 with the containment bag removed.

Referring now to the drawings wherein like reference characters designate like or corresponding parts throughout the several views, FIG. 1 shows a generally rectangular thermal storage and/or shipping container 10 closed about a sealed leak-resistant containment bag 12 in which a portion extends out one longitudinal side of container 10. As illustrated in the opened container 10 of FIG. 2, the portion of bag 12 within container 10 typically contains medical specimen tubes 14, and the extended portion contains a document 16 pertaining to the contents of tubes 14.

Container 10 comprises two complementary hollow sections 10a and 10b molded of high impact plastic with surrounding rims 18a and 18b which interengage and close tightly to form a box-like enclosure with minimal air transfer to or from the container. As best seen in FIG. 5, a flange 20 in rim 18a provides an interference fit with a recessed collar 22 in rim 18b at the four sides of section 10b. Thus, when sections 10a and 10b are manually pressed together at rims 18a and 18b, there is sufficient resilience for flange 20 to snap tightly into collar 22. Slight depressions or indentations 23 are provided on opposite sides of sections 10a and 10b for gripping and separating the sections with the fingers or thumbs.

Sections 10a and 10b include walls 28a and 28b, respectively, fixed at their perimeters to shoulders 30a and 30b in rims 18a and 18b, respectively, to form two chambers. A gel 24 within a hermetically sealed plastic pouch 26 completely fill each chamber for contiguous contact with interior sides of walls 28a and 28b, which are preferably of molded plastic like sections 10a and 10b. The exterior facing sides of walls 28a and 28b are in close proximity and have congruent centrally located indentations 32a and 32b forming a single rectangular compartment 34 sufficient in size for a snug fit of specimen tubes 14 and containment bag 12 when sections 10a and 10b are tightly close on each other at rims 18a and 18b.

The composition of gel 24 has sufficient thermal inertia for maintaining the contents of container 10 within desired temperature limits for as long as possible. For example, a slow-warming gel having a low freezing point and relatively high specific heat would be desirable for storing a frozen specimen over a long period, even though the gel itself may not be frozen. On the other hand, a slow-cooling gel would be used to keep a specimen from freezing in an extremely cold environment. A temperature indicator strip 25 is adhered to wall 28a within compartment 34 to enable display of the temperature in container 10. A suitable indicator manufactured by Hallcrest of Glenview, Ill. utilizes an adhesive strip with a row of liquid crystal squares which turn color at incrementally lower temperature.

Containment bag 12 comprises three generally congruent rectangular flexible sheets 36a, 36b, and 36c, such as of transparent polyethylene thin film, with a combined thickness permitting one portion of bag 12 to lie flat between walls 28a and 28b with specimen tubes 14 placed in compartment 34. The remaining portion weaves through the interference fit of flange 20 and collar 22 and extends from the container without diminishing the force required to manually separate the container sections 10a and 10b.

Sheets 36a, 36b and 36c are sealingly bonded together along their longitudinal edges 38 and along one edge 40 to form a tube pouch 42 and a document pouch 44 partitioned by sheet 36b. A label L, such as the Biohazard symbol required by OSHA for blood specimens, may be imprinted on the extended portion of bag 12. The other end of sheet 36b extends slightly beyond sheet 36a to form offset openings 48 and 50 in pouches 42 and 44, respectively. The other end of sheet 36c extends beyond sheet 36b an amount sufficient to form a flap 52 which can fold back, as shown in broken line in FIG. 2, and cover openings 48 and 50. The side of flap 52 which faces the openings when folded back is coated with an adhesive 54 under a peel-strip 56 to provide a leak-resistant closure to pouches 42 and 44. Adhesive 54 forms a permanent seal over openings 48 and 50, therefore each of sheets 36a, 36b and 36c is scored along a line 57, located adjacent to flap 52 when folded over openings 48 and 50, to provide a tear line for quick access to pouches 42 and 44. Other bag and sealing configurations are contemplated without departing from the fundamental inventive concepts as claimed herein.

The invention is particularly suitable for temporarily storing potentially infectious blood specimens in an insulated lock box outside a doctor's office or a clinic for pick-up after hours by a courier for delivery to a testing laboratory. For this purpose container 10 is constructed in two half sections 10a and 10b of 0.055" gage molded polystyrene plastic measuring approximately 7" long×5" wide×2⅜" deep. The sections may be a thicker gage depending on the molding process. Each half contains an eight-ounce pack of a slow-warming coolant 24 such as Cold Ice manufactured by Cold Ice, Inc., formulated to freeze at approximately −10° F.

With no specimen inside, the container is chilled, such as in a conventional household freezer, to within the approximate range of −10° F. to +10° F. preferably for a minimum of 18 to 24 hours. Before using the container, the temperature indicator 25 should indicate a temperature of +5° F. or below. The specimens are frozen separately in containment bag 12, and placed in indentation 32a or 32b of either section 10a or 10b with bag 12 lying flat and extending over one side with any warning labels and documents readily visible or accessible from without. Sections 10a and 10b are then pressed together forcing a tight snap-fit at flange 20 and collar 22. Container 10 is then deposited in the lock box for later pick-up by the courier. The courier leaves the container in the lock box, but bag 12 with the specimen therein is removed and transferred to a freezer or dry ice in the courier's van. Until the specimen is picked up, it is preserved in its frozen state by the jacket of pre-chilled slow-warming gel within the container.

Figure 6:
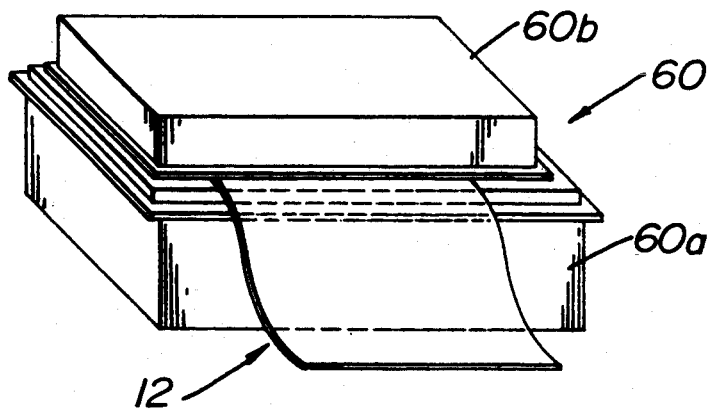
FIG. 6 is a perspective view of another embodiment of a thermal storage and/or shipping container shown closed with a containment bag extending from one side.
Figure 7:
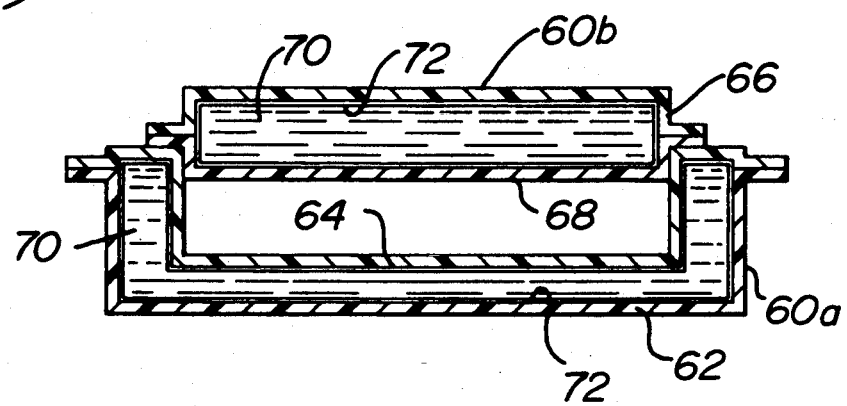
FIG. 7 represents in longitudinal cross section the container of FIG. 6 without the containment bag.
Figure 8:
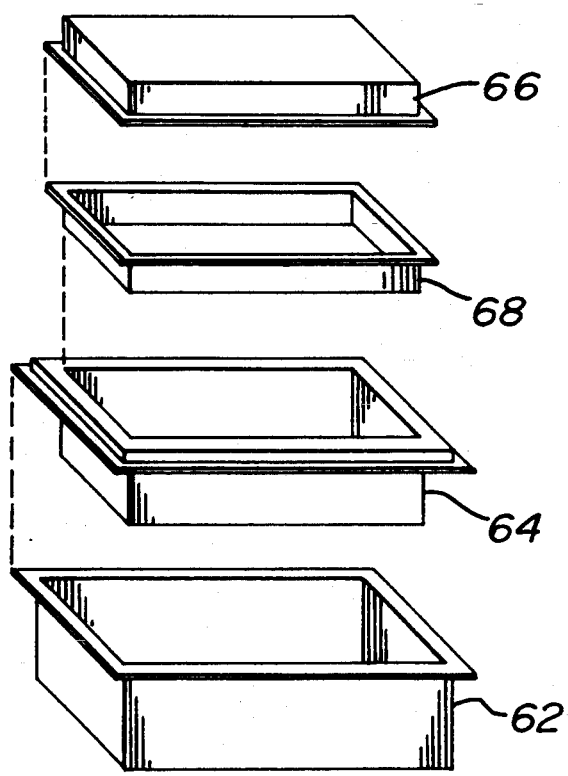
FIG. 8 is an exploded view in perspective of molded plastic sections of the container of FIG. 6.

Referring now to FIG. 6, 7 and 8, an alternate container configuration is shown which is designed to hold a variety of articles. Indicated generally by the reference number 60, it comprises a rectangular receptacle 60a for receiving the articles, and a press-fit lid 60b, each fabricated of a high-impact molded plastic with double walls. A portion of containment bag 12 extends through one side of container 60 for labeling and holding documents. More specifically, receptacle 60a includes an outer shell 62 and a inner liner 64 spaced from each other and joined at the perimeters thereof to form single chamber around the four sides and bottom of receptacle 60a. Lid 60b includes an outer shell 66 and an inner liner 68 joined along their perimeters to form an enclosed chamber. Liner 68 is sized to be removably press-fitted into the top of liner 64 with sufficient resilience to permit containment bag 12 to pass between the mating surfaces of liners 64 and 68. In a manner similar to specimen container 10, the chambers are each completely filled with a relatively high thermal inertia gel or composition 70 formulated for a desired freezing temperature and hermetically sealed in a pouch 72. A temperature indicator (not shown) is preferably attached to an inner surface of line 64.

Some of the many advantages and novel features of the invention should now be readily apparent. For example, the thermal container and containment bag combination according to the invention provides a durable and reliable, leak-resistant unit designed to comply with OSHA requirements for storing and/or shipping potentially infectious materials while holding them at a desired temperature for extended periods. The container is a useful replacement for standard dry ice containers used by medical clinics and laboratories, but is less expensive and not hazardous. Warning labels can be prominently displayed, and accompanying documents can be made readily accessible without opening the container. The container can be manufactured at relatively low costs and, when used for biological specimens, can be configured to fit into typical lock boxes used by most doctors and clinics. Since the container is made of plastic with no loose pieces, it will not absorb specimen spills, and is therefore safe and convenient for courier pick-up. The container may also be used to keep specimens from freezing during the winter by using a slow-to-cool gel.

It will be understood that various changes in the details, steps and arrangement of parts, which have been herein described and illustrated in order to explain the nature of the invention, may be made by those skilled in the art within the principle and scope of the invention as expressed in the appended claims.

I claim:

1. A thermal enclosure for storage and/or shipping articles, the enclosure comprising, in combination:

two complementary separable hollow sections having inner walls with mutually facing sides to form a compartment with surrounding edges thereof forming with each other interengagable rims securing said sections together and outer walls forming, with respective ones of said inner walls, a chamber in each of said sections;

a pre-cooled composition confined within each of said chambers, said composition having a thermal inertia sufficient for maintaining the articles in said compartment within a desired temperature range for a relatively long period; and a bag having one portion retained within said compartment and another portion weaving between said rims and extending out of said container, said one portion formed to hold the articles in said compartment.

2. An enclosure according to claim 1 wherein:
said sections are molded plastic shells; and
said rims include a flange and a collar with a resilient interference fit permitting said rims to snap together with compression of said sections.

3. An enclosure according to claim 1 wherein:
said walls include a centrally located indentation in said compartment adapted to accommodate the articles.

4. An enclosure according to claim 1 wherein:
said bag is a flexible plastic having two pouches for separately receiving the articles and other material.

5. An enclosure according to claim 1 wherein:
said composition is a refrigerant gel which freezes at approximately $-10°$ F.

6. An enclosure according to claim 1 further comprising:
depressions formed in opposite sides of at least one of said sections for gripping with the fingers or thumbs.

7. An enclosure according to claim 1 further comprising:
temperature responsive means secured to one of said exterior sides for indicating the temperature thereat.

8. A thermal storage and shipping enclosure for potentially infectious biological specimens, comprising, in combination:

two complementary separable hollow sections each having an interior wall with a surrounding edge forming with the other edge interengaged rims securing said sections together, each of said interior walls having one side facing the other one side to form a compartment therebetween, and exterior walls forming, with respective ones of said interior walls, two chambers;

a pre-cooled composition confined within each of said chambers, said composition having a thermal inertia sufficient for maintaining the specimens within a desired temperature range for a relatively long period; and a leak-resistant bag having a closed end portion retained within said compartment and an open end portion weaving between said rims and extending out of said container, said closed end portion formed to hold the specimen within said compartment, and said open end portion being sealable.

9. An enclosure according to claim 8 wherein:
said sections are molded plastic shells; and
said rims respectively include a flange and a collar with a resilient interference fit for permitting said rims to snap together with compression of said sections.

10. An enclosure according to claim 8 wherein:
said walls include a centrally located indentation in said compartment adapted to accommodate the specimen.

11. An enclosure according to claim 8 wherein:
said leak-resistant bag is a rectangular flexible thin-film plastic having two pouches for separately receiving the specimen and any accompanying documents.

12. An enclosure according to claim 8 wherein:
said composition is a refrigerant gel having a low freezing point.

13. A thermal enclosure for storing biological specimens comprising, in combination:

two hollow sections each enclosed by rectangular front, rear and four side panels, the exterior surfaces of said front panels face each other with the surrounding edges thereof forming interengagable rims securing said sections together, the interior surfaces of said front panels form, with respective ones of said rear and side panels, two chambers, and the exterior surfaces of said front panels form with each other a compartment for the specimens, said front panels each includes a centrally located indentation forming with each other in said compartment a pocket closely adapted to accommodate the specimens; and a composition confined within each of said chambers, said composition having a refrigerant coolant pre-cooled below a predetermined temperature.

14. A thermal enclosure according to claim 13 further comprising:
a leak-resistant bag having a closed end portion retained within said compartment and an open end portion weaving between said rims and extending out of said container, said closed end portion formed to hold the specimens within said compartment, and said open end portion being sealable.

15. An enclosure according to claim 13 wherein:
said sections are molded plastic shells; and
said rims include a flange and a collar with a resilient interference fit for permitting said rims to snap together with compression of said sections.

16. An enclosure according to claim 14 wherein:
said leak-resistant bag includes three congruent rectangular flexible thin-film plastic sheets joined along three sides to form two pouches for receiving the specimens and any accompanying documents, respectively.

17. An enclosure according to claim 16 further comprising:
a surface area on the closed end portion of said bag for an imprinted label.

18. An enclosure for maintaining an article at a desired temperature comprising:
two interengageable containers, each having a perimeter and containing a composition having a relatively high thermal inertia, said containers disposed adjacent each other to form interfaces with each other, and forming at the interfaces thereof a compartment for receiving the article and an interference fit around the perimeters thereof; and
a bag retained within said compartment with a portion thereof extending out of said containers, said bag formed to hold the article within said compartment.

19. An enclosure according to claim 18 wherein:
said containers are of molded plastic.

20. An enclosure according to claim 18 wherein:
said containers include a centrally located indentation at the interfaces thereof conforming said compartment with the shape of the article.

21. An enclosure according to claim 18 wherein:
said bag is of a flexible thin-film plastic formed to receive the article in separate pouches.

22. An enclosure according to claim 18 wherein:
said composition has a relatively high specific heat.

23. An enclosure according to claim 18 further comprising in combination:
temperature responsive means secured within said compartment for indicating the temperature therein.

24. A thermal enclosure for storing and/or shipping articles comprising, in combination:
two complementary hollow sections having separably interengaged rims securing said sections together, said sections each having an inner wall with a side of one wall facing a side of the other wall to form a compartment bounded by said rims, and said sections each having an outer wall forming with a respective one of said inner walls two chambers;
a pre-cooled, slow-warming composition confined within said chambers; and
a bag having one portion retained within said compartment and a remaining portion compressed between said rims and extending out of said container, said one portion formed to accommodate the article in said compartment.

25. An enclosure according to claim 24 wherein:
said sections are constructed of a molded polystyrene plastic.

26. An enclosure according to claim 24 wherein:
said composition comprise a slow-warming coolant formulated to freeze at approximately $-10°$ F.

27. A method for storing and shipping a specimen, comprising the steps of:
chilling sections of the enclosure of claim 1 to within the approximate range of $-10°$ F. to $+10°$ F. for approximately 18 to 24 hours;
separately freezing the specimens in the one portion of the bag of claim 1;
placing the one portion of the bag in one of the sections with an exposed label in the other portion of the bag extending over one side; and
pressing the sections together to force a tight snap-fit at the rims.

28. A method according to claim 27 further comprising the steps of:
depositing the enclosure in a lock-box for later pickup.

* * * * *